(12) United States Patent
Miller et al.

(10) Patent No.: US 11,220,472 B2
(45) Date of Patent: Jan. 11, 2022

(54) PROCESSES AND SYSTEMS FOR RECOVERING R1233ZD IN PURIFIED FORM

(71) Applicant: Arkema Inc., King of Prussia, PA (US)

(72) Inventors: Jay F. Miller, Downingtown, PA (US); John A. Wismer, Washington Crossing, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 16/468,416

(22) PCT Filed: Dec. 14, 2017

(86) PCT No.: PCT/US2017/066336
§ 371 (c)(1),
(2) Date: Jun. 11, 2019

(87) PCT Pub. No.: WO2018/118625
PCT Pub. Date: Jun. 28, 2018

(65) Prior Publication Data
US 2020/0010392 A1    Jan. 9, 2020

Related U.S. Application Data

(60) Provisional application No. 62/437,109, filed on Dec. 21, 2016.

(51) Int. Cl.
C07C 17/383    (2006.01)
C07C 17/386    (2006.01)
C07C 21/18     (2006.01)

(52) U.S. Cl.
CPC .......... *C07C 17/386* (2013.01); *C07C 17/383* (2013.01); *C07C 21/18* (2013.01)

(58) Field of Classification Search
None
See application file for complete search history.

(56) References Cited

U.S. PATENT DOCUMENTS

| | | |
|---|---|---|
| 6,013,846 A | 1/2000 | Wismer et al. |
| 2012/0010449 A1 | 1/2012 | Wismer et al. |
| 2012/0296127 A1 | 11/2012 | Cottrell et al. |
| 2013/0131404 A1 | 5/2013 | Hulse et al. |
| 2013/0211154 A1 | 8/2013 | Cottrell et al. |
| 2014/0231240 A1 | 8/2014 | Wismer et al. |

*Primary Examiner* — Medhanit W Bahta
(74) *Attorney, Agent, or Firm* — Steven D. Boyd

(57) ABSTRACT

Aspects of the invention relate to systems and processes for recovering R1233zd in purified form from compositions additionally comprising hydrogen fluoride. In accordance with one aspect, the invention provides a process that includes separating a feed stream comprised of hydrogen fluoride and R1233zd using azeotropic distillation in a first distillation column to produce a first distillate stream comprised of hydrogen fluoride and R1233zd and a first bottoms stream consisting essentially of hydrogen fluoride. The first distillation column is operated at a first pressure. The process further includes separating the first distillate stream using azeotropic distillation in a second distillation column to produce a second distillate stream comprised of hydrogen fluoride and R1233zd and a second bottoms stream consisting essentially of R1233zd. The second distillation column is operated at a second pressure that may be different than the first pressure of the first distillation column.

25 Claims, 3 Drawing Sheets

PROCESSES AND SYSTEMS FOR RECOVERING R1233ZD IN PURIFIED FORM

This present application is the national phase under 35 USC § 371 of prior PCT International Application Number PCT/US2017/066336 filed Dec. 14, 2017 which designated the United States of America and claimed priority to U.S. Provisional patent application Ser. No. 62/437,109 filed December 21, 2016.

FIELD OF THE INVENTION

This disclosure relates to processes and systems for recovering R1233zd in purified form, and more particularly recovering isomers of R1233zd from compositions additionally comprising hydrogen fluoride.

BACKGROUND OF THE INVENTION

R1233zd is a useful compound for the production of various products. For example, R1233zd may be used as an intermediate to form 1,1,1,3,3-pentafluoropropane, which is known to have utility as a foam blowing agent and a refrigerant.

One way of manufacturing R1233zd involves reacting 1,1,3,3-tetrachloro-2-propene (hereinafter "1230za") with an excess of hydrogen fluoride (HF). There is a long standing need for improved systems and process for recovering R1233zd in a purified form from compositions comprising R1233zd and hydrogen fluoride.

SUMMARY OF THE INVENTION

Aspects of the invention relate to systems and processes for recovering R1233zd in purified form from compositions additionally comprising hydrogen fluoride.

In accordance with one aspect, the invention provides a process that includes separating a feed stream comprised of hydrogen fluoride and R1233zd using azeotropic distillation in a first distillation column to produce a first distillate stream comprised of hydrogen fluoride and R1233zd and a first bottoms stream consisting essentially of hydrogen fluoride. The first distillation column is operated at a first pressure. The process further includes separating the first distillate stream using azeotropic distillation in a second distillation column to produce a second distillate stream comprised of hydrogen fluoride and R1233zd and a second bottoms stream consisting essentially of R1233zd. The second distillation column is operated at a second pressure that is different than the first pressure of the first distillation column; for example, the second pressure may be lower than the first pressure.

Various aspects of the invention may be summarized as follows:

Aspect 1: A process for recovering R1233zd in purified form from compositions additionally comprising hydrogen fluoride:

separating a feed stream comprised of hydrogen fluoride and R1233zd using azeotropic distillation in a first distillation column to produce a first distillate stream comprised of hydrogen fluoride and R1233zd and a first bottoms stream consisting essentially of hydrogen fluoride, the first distillation column operating at a first pressure;

separating the first distillate stream using azeotropic distillation in a second distillation column to produce a second distillate stream comprised of hydrogen fluoride and R1233zd and a second bottoms stream consisting essentially of R1233zd, the second distillation column operating at a second pressure.

Aspect 2: The process of Aspect 1, wherein the feed stream has a molar ratio of hydrogen fluoride to R1233zd of from 4:1 to 12:1.

Aspect 3: The process of Aspect 2, wherein the molar ratio of hydrogen fluoride to R1233zd is from 6:1 to 10:1.

Aspect 4: The process of Aspect 3, wherein the molar ratio of hydrogen fluoride to R1233zd is about 8:1.

Aspect 5: The process of any of Aspects 1-4, wherein the first pressure is at least 500% greater than the second pressure.

Aspect 6: The process of Aspect 5, wherein the first pressure is at least 750% greater than the second pressure.

Aspect 7: The process of Aspect 6, wherein the first pressure is at least 1000% greater than the second pressure.

Aspect 8: The process of any of Aspects 1-7, wherein the first pressure is at least 80 psi greater than the second pressure.

Aspect 9: The process of Aspect 8, wherein the first pressure is at least 100 psi greater than the second pressure.

Aspect 10: The process of Aspect 9, wherein the first pressure is at least 120 psi greater than the second pressure.

Aspect 11: The process of any of Aspects 1-10, further comprising reacting hydrogen fluoride with 1230za in a reactor to produce a reactor outlet stream comprising hydrochloric acid, hydrogen fluoride, R1233zd, and trace impurities.

Aspect 12: The process of Aspect 11, further comprising removing hydrochloric acid from the reactor outlet stream to produce the feed stream, wherein the feed stream has a composition essentially free of hydrochloric acid.

Aspect 13: The process of Aspect 11 or 12, wherein the first bottoms stream is recycled into the reactor.

Aspect 14: The process of any of Aspects 1-13, wherein the second distillate stream is recycled into the feed stream.

Aspect 15: The process of any of Aspects 1-14, wherein the R1233zd of the feed stream consists essentially of R1233zd(e).

Aspect 16: The process of Aspect 15, wherein the first bottoms stream is comprised of at least 98% by weight hydrogen fluoride.

Aspect 17: The process of Aspect 15, wherein the second bottoms stream is comprised of at least 90% by weight R1233zd.

Aspect 18. The process of Aspect 17, wherein the second bottoms stream is comprised of at least 95% by weight R1233zd.

Aspect 19: The process of Aspect 15, wherein the first pressure is from about 150 to about 250 psia and the second pressure is from about 15 to about 50 psia.

BRIEF DESCRIPTION OF THE DRAWINGS

The invention is best understood from the following detailed description when read in connection with the accompanying drawings, with like elements having the same reference numerals. According to common practice, various features of the drawings are not drawn to scale unless otherwise indicated. On the contrary, the dimensions of the various features may be expanded or reduced for clarity. Included in the drawings are the following figures.

DETAILED DESCRIPTION OF THE INVENTION

Aspects of the invention are directed to processes and systems for recovering R1233zd in purified form, and more particularly recovering isomers of 1-chloro-3,3,3-trifluoropropene (hereinafter "R1233zd") from compositions additionally comprising hydrogen fluoride (hereinafter "HF").

As previously mentioned, R1233zd may be economically produced by reacting 1,1,3,3-tetrachloro-2-propene (1230za) with excess HF. The present inventors have discovered embodiments of the invention which enable the economic recovery of R1233zd, in purified form, from a composition that includes R1233zd and HF, such as a composition obtained as a reaction product from the aforementioned reaction. Thus, by using aspects of the invention, R1233zd may be economically produced and recovered, such that R1233zd may be further processed or employed in a purified form.

Figure 1:
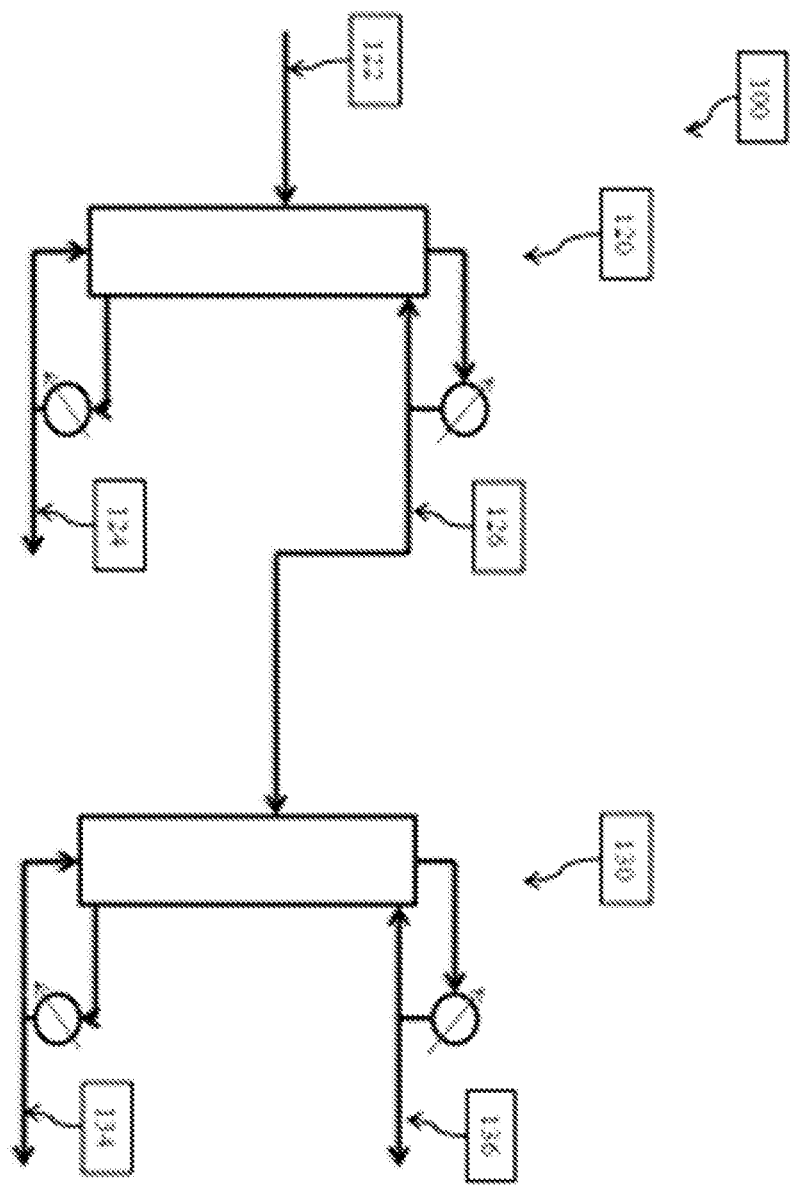
FIG. 1 is a schematic of a separation system for recovering R1233zd in purified form from compositions including hydrogen fluoride in accordance with aspects of the invention.

FIG. 1 illustrates a separation system 100 for recovering R1233zd in purified form from compositions including HF according to aspects of the invention. As a general overview, separation system 100 includes a first distillation column 120 and a second distillation column 130.

First distillation column 120 is adapted for recovering R1233zd from compositions additionally including hydrogen fluoride, using azeotropic distillation (i.e., a distillate stream is taken overhead which is an azeotrope of R1233zd and HF). As illustrated in FIG. 1, first distillation column 120 receives feed stream 122, which contains R1233zd and HF (with the HF generally being in molar excess relative to the R1233zd). The composition of feed stream 122 may have a molar ratio of HF to R1233zd, e.g., from 4:1 to 12:1, and/or preferably from 6:1 to 10:1 or from 7:1 to 9:1. In one embodiment, feed stream 122 has a molar ratio of HF to R1233zd that is about 8:1. Additionally and/or alternatively, the R1233zd component of feed stream 122 may be substantially composed of R1233zd(e), such that the R1233zd component is, e.g., 70% or more R1233zd(e) by weight, 80% or more R1233zd(e) by weight, 90% or more R1233zd(e) by weight, and/or 95% or more R1233zd(e) by weight. For example, the R1233zd of feed stream 122 may consist essentially of R1233zd(e). In one embodiment, the R1233zd of feed stream 122 consists of R1233zd(e) and trace components.

First distillation column 120 may be configured as a packed bed column or configured to have a plurality of sieve trays or the like. In one embodiment, first distillation column 120 has twenty-five trays or an equivalent thereof, with the twelfth tray from the top of first distillation column 120 being the feed tray. First distillation column 120 may be operated, in various exemplary embodiments of the invention, at a pressure of, e.g., 50 psia to 300 psia, 100 psia to 250 psia, and/or 150 psia to 250 psia. In one embodiment, first distillation column 120 is operated at a pressure of about 200 psia.

As further discussed below, first distillation column 120 is configured to facilitate recovery of R1233zd by producing a bottoms stream 124, which has a composition including HF, and a distillate stream 126, which has an azeotropic composition including R1233zd and HF. Preferably, bottoms stream 124 has a composition that is substantially pure HF, e.g., a composition of 90% or more HF by weight, more preferably 95% or more HF by weight, more preferably 96.5% or more HF by weight, more preferably 98% or more HF by weight, more preferably 99% or more HF by weight, more preferably 99.5% or more HF by weight, more preferably 99.8% or more HF by weight. In one embodiment, bottoms stream 124 has an essentially pure composition of HF. In another embodiment, bottoms stream 124 has a composition consisting of HF and trace impurities. Distillate stream 126 may have an azeotropic composition with a molar ratio of HF to R1233zd that is less than 3:1, preferably less than 2.5:1, and more preferably less than 2:1. For example, distillate stream 126 may have an azeotropic composition with a molar ratio of HF to R1233zd from 0.5:1 to 3:1, from 1:1 to 2.5:1, or from 1.5 to 2.0. In one embodiment, distillate stream 126 has a molar ratio of HF to R1233zd of about 1.86:1.

Second distillation column 130 is also adapted for recovering R1233zd, using azeotropic distillation, from compositions that include R1233zd and hydrogen fluoride, e.g., from the azeotropic composition of distillate stream 126 withdrawn from first distillation column 120. Second distillation column 130 may be configured as a packed bed column or to have a plurality of sieve trays or the like. In one embodiment, second distillation column 130 has thirty trays or an equivalent thereof. Distillate stream 126 may be introduced into second distillation column 130 using, for example, tray 14, 15 or 16 as a feed tray. Second distillation column 130 may be operated at a pressure of, e.g., 14.6 psia to 100 psia, 15 psia to 75 psia, and/or 15 psia to 25 psia. In one embodiment, second distillation column 130 is operated at a pressure of about 20 psia.

Second distillation column 130 is configured to recover R1233zd in bottoms stream 134 and produce a distillate stream 136 having a composition that includes HF. Second distillation column 120 may be configured to optimize the amount of R1233zd recovered in bottoms stream 134 or configured to optimize the purity of R1233zd recovered in bottoms stream 134. Preferably, bottoms stream 134 has a composition of substantially pure R1233zd, e.g., a composition of 90% or more R1233zd by weight, more preferably 95% or more R1233zd by weight, more preferably 96.5% or more R1233zd by weight, more preferably 98% or more R1233zd by weight, more preferably 99% or more R1233zd by weight, more preferably 99.5% or more R1233zd by weight, more preferably 99.8% or more R1233zd by weight. In one embodiment, bottoms stream 134 has an essentially pure composition of R1233zd. In another embodiment, bottoms stream 134 has a composition consisting of R1233zd and trace impurities. The R1233zd composition of bottoms stream 134 may consists essentially of R1233zd(e) (e.g., the recovered R1233zd is at least 99%, at least 99.5% or at least 99.9% by weight R1233zd(e)). In one embodiment of the invention, the recover R1233zd consists of R1233zd(e). In another embodiment, however, distillate stream 134 is sent to another distillation column to separate the R1233zd(e) from R1233zd(z).

Distillate stream 136 has a molar ratio of HF to R1233zd, e.g., from 5:1 to 1:4, preferably from 4:1 to 1:2, and preferably from 3:1 to 1:1. In one embodiment, distillate stream 136 has an azeotropic composition having a molar ratio of HF to R1233zd of about 2:1. In various embodiments of the invention, distillate stream 136 contains a molar ratio of HF:R1233zd of from about 1:1 to about 5:1, about 1.5:1 to about 4:1, or about 1.75:1 to about 2.5:1.

By employing first distillation column 120 and second distillation column 130, separation system 100 advantageously produces bottoms stream 124 having a composition of substantially pure HF and bottoms stream 134 having a composition of substantially pure R1233zd. Distillation column 120 is configured to operate at a pressure higher than second distillation column 130. For example, first distillation column 120 may be operated at a pressure that is 80 psi greater than the operating pressure of second distillation column 130. In one embodiment, first distillation column 120 is operated at a pressure that is at least 100 psi greater than the operating pressure of second distillation column 130. In another embodiment, first distillation column 120 is operated at a pressure that is at least 120 psi greater than the operating pressure of second distillation column 130.

The difference in operating pressures of first distillation column 120 and second distillation column 130 may be optimized to produce a desired amount and purity of R1233zd and/or HF. For example, first distillation column 120 may be operated at a pressure that is at least 500% greater than the operating pressure of second distillation column 130. In one embodiment, first distillation column 120 is operated at a pressure that is at least 750% greater than the operating pressure of second distillation column 130. Yet, in another embodiment, first distillation column 120 is operated at a pressure that is at least 1000% greater than the operating pressure of second distillation column 130.

Figure 2:
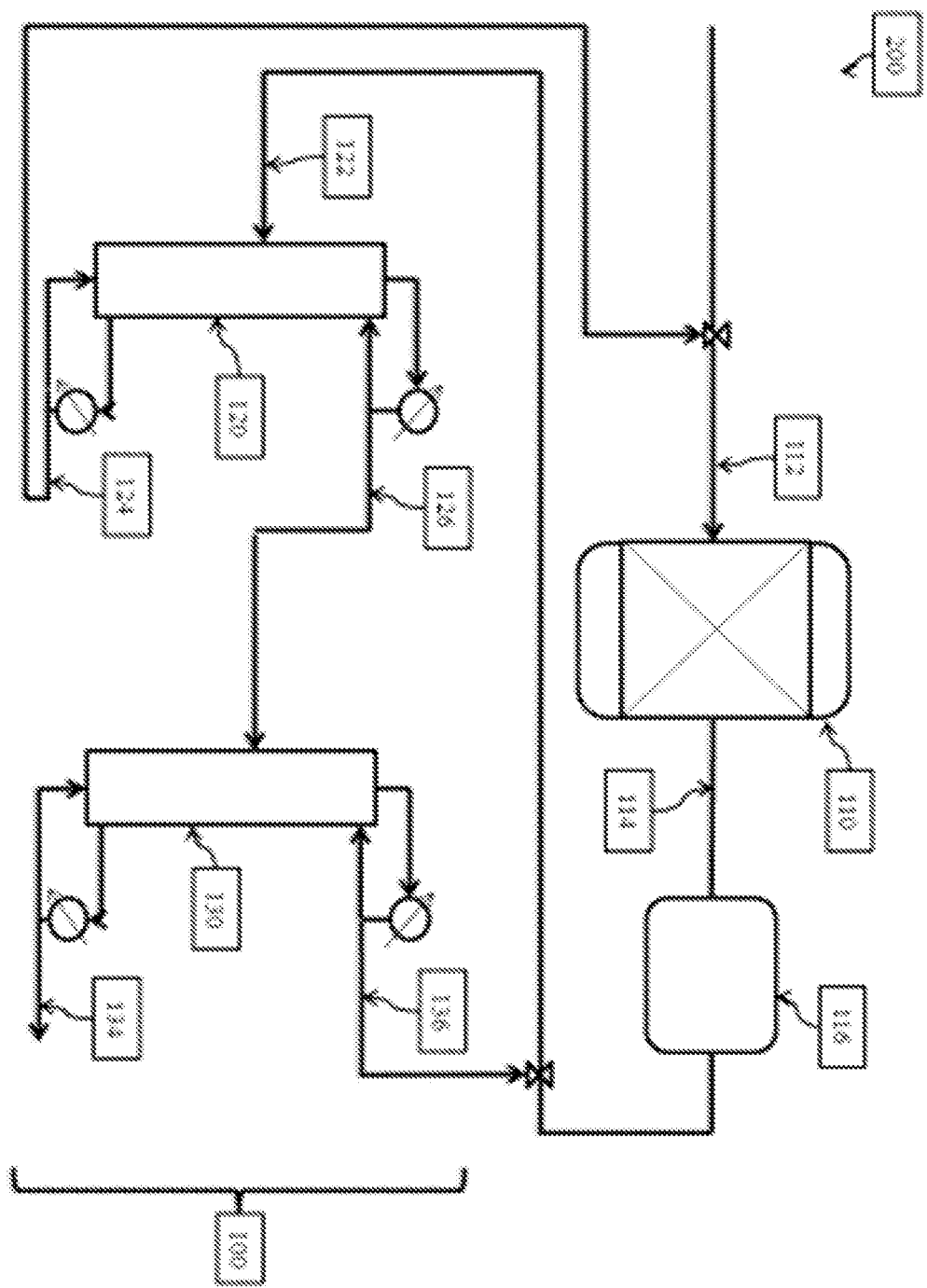
FIG. 2 is a schematic of a manufacturing system employing a reactor for producing R1233zd and the separation system of FIG. 1 according to aspects of the invention.

FIG. 2 illustrates a manufacturing system 200 for producing and recovering R1233zd according to aspects of the invention. As a general overview, manufacturing system 200 includes reactor 110, first distillation column 120, and second distillation column 130. Manufacturing system 200 is illustrated as employing separation system 100. Accordingly, where manufacturing system 200 utilizes features/system equipment of separation system 100, the same reference numbers are applied as those in FIG. 1.

Reactor 110 is configured to produce R1233zd from 1230za and HF. For example, reactor 110 may receive a reactor feed stream 112 having a composition of 1230za, HF, and trace impurities and produce a reactor outlet stream 114 having a composition of R1233zd, HF, and HCl. Reactor outlet stream 114 may be fed to one or more processing equipment 116, e.g., a knock out drum, distillation column, filtration, etc., to remove or substantially reduce HCl from feed stream 122. In one embodiment, hydrochloric acid is removed from reactor outlet stream 114, such that feed stream 122 has a composition essentially free of hydrochloric acid. Although reactor 110 is configured to produce R1233zd from 1230za and HF in FIG. 2, reactor 110 may be configured to produce R1233zd by way of other reaction mechanisms and/or using other reactants.

Manufacturing system 200 may be configured to recycle compounds recovered from separation system 100 to reactor feed stream 112 and/or feed stream 122 of first distillation column 120. For example, first bottoms stream 124 may be recycled into reactor 110 by way of reactor feed stream 112. Distillate stream 136 of second distillation column 130, which has an azeotropic composition of HF and R1233zd, may be recycled into feed stream 122 of first distillation column 120.

Figure 3:
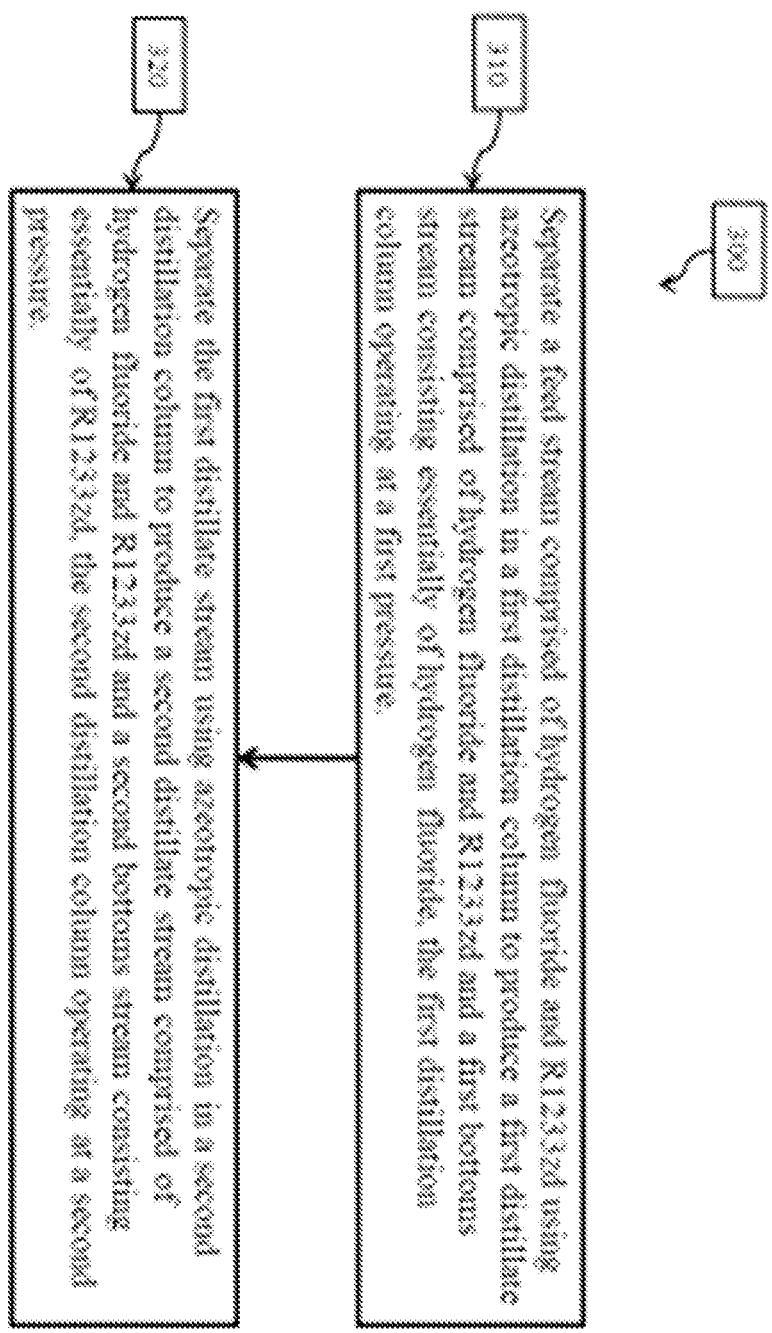
FIG. 3 is a flow chart of a process for recovering R1233zd in purified form from compositions including hydrogen fluoride in accordance with aspects of the invention.

FIG. 3 illustrates a flow chart of a process for recovering R1233zd in purified form from compositions including hydrogen fluoride in accordance with aspects of the invention.

In step 310, a feed stream comprised of HF and R1233zd is separated using azeotropic distillation. A first distillation column (e.g., first distillation column 120) may be used to produce a first distillate stream comprised of HF and R1233zd and a first bottoms stream consisting essentially of HF. The first distillation column may be operated at parameters (e.g., a first pressure) to optimize the purity or amount of HF in the bottoms stream and/or the R1233zd in the first distillate stream.

In step 320, the first distillate stream is separated using azeotropic distillation. A second distillation column (e.g., second distillation column 130) may be used to produce a second distillate stream comprised of HF and R1233zd and a second bottoms stream consisting essentially of R1233zd. The second distillation column may be operated at parameters (e.g., a second pressure) to optimize the purity or amount of R1233zd in the bottoms stream and/or the HF in the second distillate stream.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the curable composition or process. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A process for recovering R1233zd (1-chloro-3,3,3-trifluoropropene) in purified form from compositions comprising hydrogen fluoride comprising:

separating a feed stream comprised of hydrogen fluoride and R1233zd (1-chloro-3,3,3-trifluoropropene) in a molar ratio of hydrogen fluoride to R1233zd (1-chloro-3,3,3-trifluoropropene) of from 4:1 to 12:1, using azeotropic distillation in a first distillation column to produce a first distillate stream comprised of hydrogen fluoride and R1233zd (1-chloro-3,3,3-trifluoropropene) and a first bottoms stream consisting essentially of hydrogen fluoride, the first distillation column operating at a first pressure at least 500% greater than a second pressure;

separating the first distillate stream using azeotropic distillation in a second distillation column to produce a second distillate stream comprised of hydrogen fluoride and R1233zd and a second bottoms stream consisting essentially of R1233zd (1,1,1-trifluoro-3-chloro-2-propene), the second distillation column operating at the second pressure.

2. The process of claim 1, wherein the molar ratio of hydrogen fluoride to R1233zd (1-chloro-3,3,3-trifluoropropene) in the feed stream is from 6:1 to 10:1.

3. The process of claim 1, wherein the molar ratio of hydrogen fluoride to R1233zd (1-chloro-3,3,3-trifluoropropene) in the feed stream is about 8:1.

4. The process of claim 1, wherein the first pressure is at least 750% greater than the second pressure.

5. The process of claim 4, wherein the first pressure is at least 1000% greater than the second pressure.

6. The process of claim 1, wherein the first pressure is at least 80 psi greater than the second pressure.

7. The process of claim 6, wherein the first pressure is at least 100 psi greater than the second pressure.

8. The process of claim 7, wherein the first pressure is at least 120 psi greater than the second pressure.

9. The process of claim 1, further comprising reacting hydrogen fluoride with 1230za (1,1,3,3-tetrachloro-2-propene) in a reactor to produce a reactor outlet stream comprising hydrochloric acid, hydrogen fluoride, R1233zd (1-chloro-3,3,3-trifluoropropene), and trace impurities.

10. The process of claim 9, further comprising removing hydrochloric acid from the reactor outlet stream to produce the feed stream, wherein the feed stream has a composition essentially free of hydrochloric acid.

11. The process of claim 9, wherein the first bottoms stream is recycled into the reactor.

12. The process of claim 1, wherein the second distillate stream is recycled into the feed stream.

13. The process of claim 1, wherein the first bottoms stream is comprised of at least 98% by weight hydrogen fluoride.

14. The process of claim 1, wherein the second bottoms stream is comprised of at least 90% by weight R1233zd (1-chloro-3,3,3-trifluoropropene).

15. The process of claim 14, wherein the second bottoms stream is comprised of at least 95% by weight R1233zd (1-chloro-3 ,3 ,3-trifluoropropene).

16. A process for recovering R1233zd (1-chloro-3,3,3-trifluoropropene) in purified form from compositions comprising hydrogen fluoride comprising:

separating a feed stream comprised of hydrogen fluoride and R1233zd (1-chloro -3,3,3-trifluoropropene) in a molar ratio of hydrogen fluoride to R1233zd (1-chloro-3,3,3-trifluoropropene) of from 4:1 to 12:1, using azeotropic distillation in a first distillation column to produce a first distillate stream comprised of hydrogen fluoride and R1233zd (1-chloro-3,3,3-trifluoropropene) and a first bottoms stream consisting essentially of hydrogen fluoride, the first distillation column operating at a first pressure of from about 150 to about 250 psi;

separating the first distillate stream using azeotropic distillation in a second distillation column to produce a second distillate stream comprised of hydrogen fluoride and R1233zd and a second bottoms stream consisting essentially of R1233zd (1,1,1-trifluoro-3-chloro-2-propene), the second distillation column operating at a second pressure from about 15 to about 25 psi.

17. The process of claim 16, wherein the molar ratio of hydrogen fluoride to R1233zd (1-chloro-3,3,3-trifluoropropene) in the feed stream is from 6:1 to 10:1.

18. The process of claim 16, wherein the molar ratio of hydrogen fluoride to R1233zd (1-chloro-3,3,3-trifluoropropene) in the feed stream is about 8:1.

19. The process of claim 16, further comprising reacting hydrogen fluoride with 1230za (1,1,3,3-tetrachloro-2-propene) in a reactor to produce a reactor outlet stream comprising hydrochloric acid, hydrogen fluoride, R1233zd (1-chloro-3,3,3-trifluoropropene), and trace impurities.

20. The process of claim 19, further comprising removing hydrochloric acid from the reactor outlet stream to produce the feed stream, wherein the feed stream has a composition essentially free of hydrochloric acid.

21. The process of claim 19, wherein the first bottoms stream is recycled into the reactor.

22. The process of claim 16, wherein the second distillate stream is recycled into the feed stream.

23. The process of claim 16, wherein the first bottoms stream is comprised of at least 98% by weight hydrogen fluoride.

24. The process of claim 16, wherein the second bottoms stream is comprised of at least 90% by weight R1233zd (1-chloro-3,3,3-trifluoropropene).

25. The process of claim 24, wherein the second bottoms stream is comprised of at least 95% by weight R1233zd (1-chloro-3,3,3-trifluoropropene).

\* \* \* \* \*